United States Patent [19]
Nerella et al.

[11] Patent Number: 6,129,931
[45] Date of Patent: Oct. 10, 2000

[54] CONTROLLED-RELEASE, DRUG-DELIVERY TABLETED COMPOSITION INCLUDING A COMPLEX BETWEEN POLY(MALEIC DIACID-ALKYL VINYL ETHER) AND POLYVINYLPYRROLIDONE

[75] Inventors: Nadhamuni G. Nerella, Wayne; Herbert W. Ulmer, Hoboken; Sibu Chakrabarti, Randolph; Gregory Du Browny, Garfield, all of N.J.

[73] Assignee: ISP Investments Inc., Wilmington, Del.

[21] Appl. No.: 09/146,422

[22] Filed: Sep. 3, 1998

[51] Int. Cl.[7] .............................. A61K 9/22; A61K 9/14; A61K 47/30

[52] U.S. Cl. .......................... 424/468; 424/464; 424/465; 424/484; 424/486; 514/772.2; 514/772.3

[58] Field of Search ...................... 424/464, 468, 424/465, 484, 486; 514/772.2, 772.3

[56] References Cited

U.S. PATENT DOCUMENTS 5,066,495  11/1991  Moro et al. .

FOREIGN PATENT DOCUMENTS

| 0 207 638 | 1/1987 | European Pat. Off. . |
| 61-017 510 | 1/1986 | Japan . |
| 1-294 627 | 11/1989 | Japan . |

*Primary Examiner*—Thurman K. Page
*Assistant Examiner*—Brian K. Seidleck
*Attorney, Agent, or Firm*—Walter Katz; William J. Davis; Marilyn J. Maue

[57] ABSTRACT

A pH-dependent, controlled-release, drug delivery composition is described herein which includes:

(a) a complex between poly(maleic diacid-alkyl vinyl ether) and polyvinylpyrrolidone, or their equivalents, and (b) an effective amount of a pharmaceutical medicament.

6 Claims, 2 Drawing Sheets

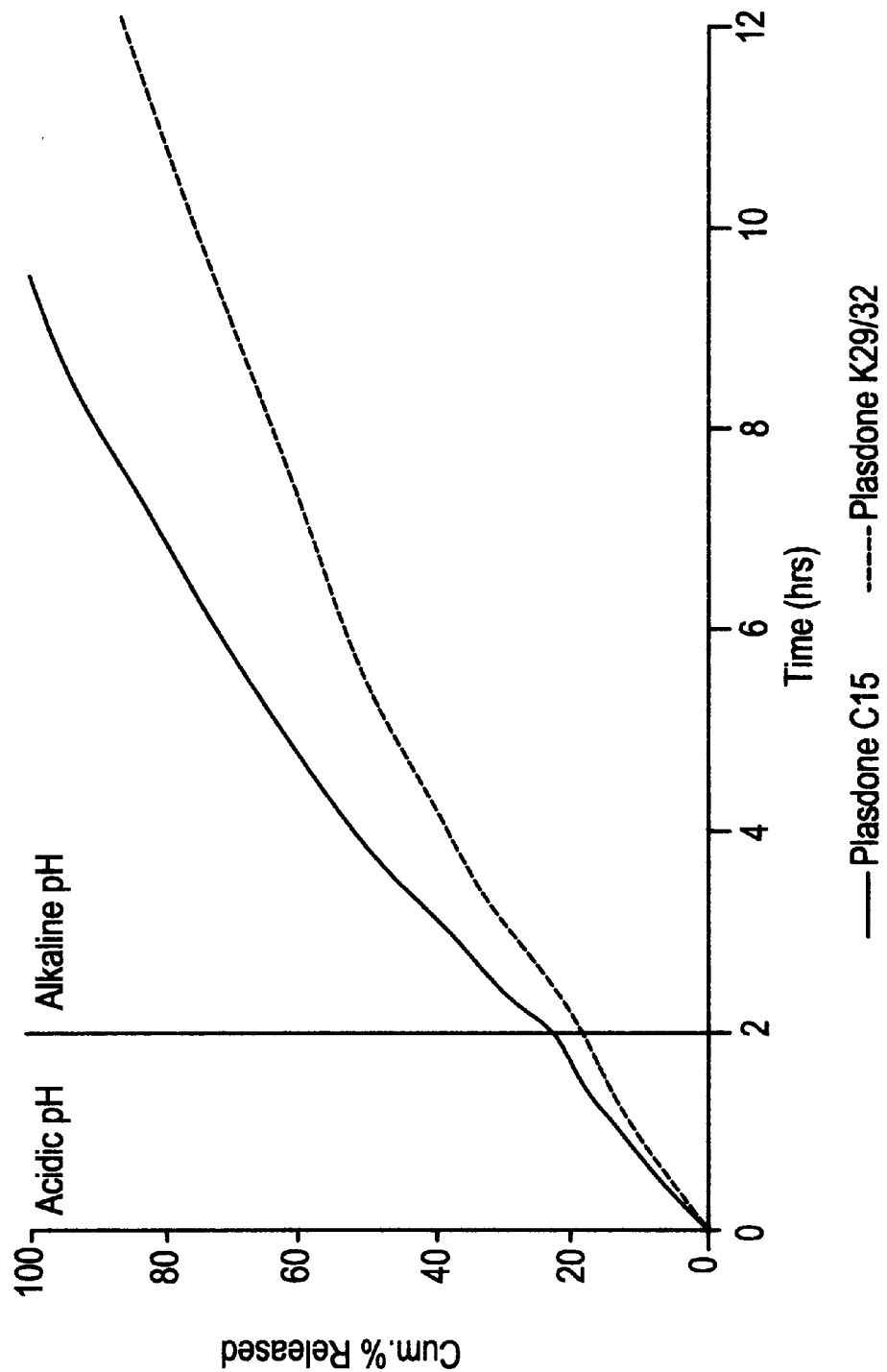

CONTROLLED-RELEASE, DRUG-DELIVERY TABLETED COMPOSITION INCLUDING A COMPLEX BETWEEN POLY(MALEIC DIACID-ALKYL VINYL ETHER) AND POLYVINYLPYRROLIDONE

BACKGROUND OF THE INVENTION

1. Field of the Invention

This invention relates to controlled-release, drug-delivery compositions, and, more particularly, to compositions which contain a hydrogen-bonded complex between two polymers for predetermining the dissolution of the drug therein in acid and alkaline solutions.

2. Description of the Prior Art

Controlled-release, drug-delivery compositions are well-known in the art. However, controlled-release tablets which can deliver a drug to the intestine without disintegrating in the gastric area require a specially designed gastric-resistant coating. Thereon typically, application of such coatings involves several processes using expensive equipment.

Accordingly, it is an object of this invention to provide a drug-delivery composition which is insoluble in aqueous acidic solution and dissolves only slowly under alkaline conditions.

Another object herein is to provide a tableted compositions having such controlled release of drugs therein, which can be made conveniently by direct compression or wet granulation techniques.

A composition such as described herein is considered pH sensitive and can be modified effectively to release the drug contents either immediately or in a controlled manner, under alkaline conditions.

Specifically, the system described herein, can function in two modes: (a) substantially no drug-release is exhibited in acidic, conditions (<20% of the drug is released in 2 hours) and controlled release of the drug occurs in alkaline conditions, (an additional 60% of the drug is released in 8 hours or more); (b) a pH-immediate mode wherein some of the drug is released in acid (<20% in 2 hours) and immediate release of the drug in alkaline conditions (an additional 60% in 2–3 hours or less).

These and other objects and features of the invention will be made apparent from the following description.

SUMMARY OF THE INVENTION

What has been discovered herein is that a hydrogen-bonded complex is formed in water between (a) a copolymer of the diacid form of maleic anhydride and an alkyl vinyl ether, e.g. methylvinyl ether, and (b) a polymer of vinylpyrrolidone, which is substantially insoluble in acid solution and only slowly dissociable under alkaline conditions. The presence of this complex in a drug formulation provides oral, pH-sensitive drug release, in both the pH-modified and pH-immediate drug-delivery modes.

In practice, the tableted composition of the invention also includes one or more pharmaceutically acceptable excipients.

BRIEF DESCRIPTION OF THE DRAWINGS

FIG. 2 is a similar graphical representation for Composition 9 herein (Gantrez MS 955) with theophylline as the model drug therein.

DETAILED DESCRIPTION OF THE INVENTION

Figure 1:
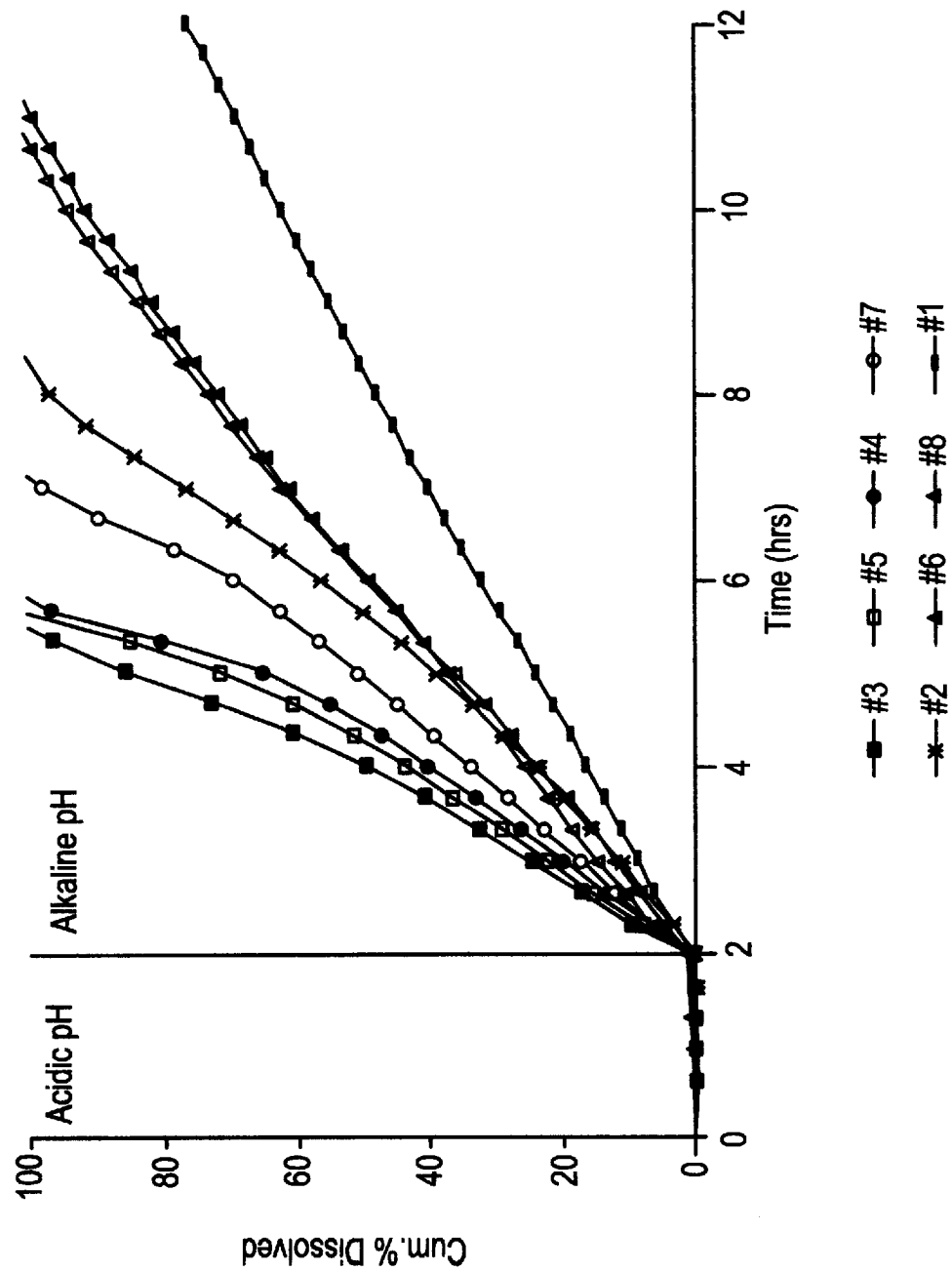
FIG. 1 is a graphical representation of % of drug released vs. time in both acid and alkaline solutions for, drug-delivery tablet compositions. Compositions 1–8 contain Naproxen sodium as the model drug therein.

In accordance with the invention, pH-sensitive drug-delivery compositions are provided which are completely or substantially insoluble in acid solution and only soluble under alkaline conditions. The inventive component of such compositions is a hydrogen-bonded complex between for example, the copolymer of maleic acid (MA) and an alkyl vinyl ether (AVE) and plasdone (polyvinylpyrrolidone (PVP)). Suitably, the compositions herein are formulated into an oral dosage form, such as a tablet, by direct compression, high shear or fluid-bed, wet granulation of its components. The desired complex between MA-MVE and PVP is formed during granulation or in situ in the water-medium, or during tablet dissolution.

Since the complex of the invention does not dissociate in aqueous acid solution, the medicinal composition does not release any substantial amount of drug into the acid portion of the body (the gastric area), even at a pH of 1.2. Furthermore, the complex dissociates only slowly under alkaline conditions, e.g. a pH of 7.4, and, accordingly, the drug is released only slowly where the body is in an alkaline condition where the rate of dissociation of the complex is determined by the extent of hydration of the complex under such alkaline conditions. The rate of dissolution can be controlled by the ratio of MA/MVE to PVP and the molecular weight of PVP.

Two modes of controlled-release operation are provided for formulations containing this hydrogen-bonded complex, namely, (1) a pH-immediate mode, wherein substantially no drug is released in acid (<20% in 2 hours), and only immediate release of the drug in alkaline solution (an additional 60% in 2–3 hours or less); and (2) a pH-modified system wherein only a small amount of drug is released in acid (<20% in 2 hours), followed by controlled release of the remaining drug in alkaline solution (an additional 60% in 8 hours or more).

The hydrogen-bonded complex of the invention is formed between (1) two polymer components, namely, maleic anhydride (MAn), or its equivalent, such as maleic acid (MA), a maleic anhydride half-ester (MAn-½ E); or their equivalents, and salts thereof; of any desirable molecular weight or K-value; and as uncrosslinked or crosslinked polymers; and (2) a polymer of vinylpyrrolidone, or its equivalent, e.g. (polyvinylpyrrolidone (PVP)), or copolymers of PVP with other comonomers, e.g. vinyl acetate, and the like; uncrosslinked or crosslinked equivalents. The preferred hydrogen-bonded complex of the invention is formed in situ in water between MA and Plasdone K-29/32 (uncrosslinked), at a molar ratio of about 1:1.

The amount of the complex incorporated into the drug formulation may vary widely; generally about 30–70% by weight, preferably about 50% is used in such compositions. This amount is dependent on the desired drug release profile.

To illustrate the invention, a series of controlled-release, drug delivery studies were carried out using different model drugs in the formulation. For example, Naproxen sodium was used as the model drug in Study A, and the compositions in the form of tablets of hardness of 10–12 KP were prepared by fluid bed granulation of the drug, MA (Gantrez® S-97 (ISP) and PVP (Plasdone® C-15 (ISP), using varying amounts of each in a 1:1 molar ratio. Calcium sulfate was included in the granulation step as an ionotropic agent to enhance the binding strength of the complex.

These formulations are indicated as Examples 1–8 in Table 1 below, and FIG. 1 shows the extent of drug released from the tablets in acid (0.1 N HCl, pH 1.2) and in an alkaline medium (phosphate buffer, pH 7.4). Tablet dissolution studies were conducted in a USP Type I apparatus.

TABLE 1

| Example No. | Naproxen Sodium (%) | Gantrez S97 (%) | Plasdone C15 (%) | Calcium Sulfate (%) | Magnesium Stearate (%) |
|---|---|---|---|---|---|
| 1 | 39.8 | 30.37 | 19.38 | 9.95 | 0.5 |
| 2 | 49.75 | 30.37 | 19.38 | 0 | 0.5 |
| 3 | 59.7 | 18.22 | 11.63 | 9.95 | 0.5 |
| 4 | 59.7 | 24.30 | 15.50 | 0 | 0.5 |
| 5 | 59.7 | 21.26 | 13.56 | 4.975 | 0.5 |
| 6 | 44.775 | 30.37 | 19.38 | 4.975 | 0.5 |
| 7 | 54.725 | 27.34 | 17.44 | 0 | 0.5 |
| 8 | 49.75 | 24.30 | 15.50 | 9.95 | 0.5 |

The results in FIG. 1 shows that in the acid medium the test tablets did not dissolve over a period of 2 hours, and that they dissolved at varying rates in alkaline solutions during 12 hours. Example 1, which contained about 50% of the complex, and 9.95% of calcium sulfate dissolved the slowest under alkaline conditions. Example 3, which contained only about 30% of the complex dissolved the fastest in the alkaline medium.

While Examples 3–5 show pH-immediate type drug release, Examples 1, 2, 6–8 exhibit pH-modified type of drug release.

Study B below (Example 9) was formulated with 40% of Gantrez® MS955 (the disodium salt of MAn-methyl vinyl ether) and Plasdone C-15 and Plasdone K 29/32 (PVP), granulated with 50% of theophylline as the model drug. The composition of the formulation is given in Table 2 below.

TABLE 2

| Theophylline | 50% |
|---|---|
| Gantrez MS955 + Plasdone | 40% |
| Calcium Sulfate | 9.5% |
| Magnesium Stearate | 0.5% |

FIG. 2 shows the cumulative % drug released over 12 hours in acid and alkaline conditions. The results are consistent with a pH-modified release system.

Example C used propranolol HCl as the model drug in a tablet containing 40% of the complex formed between Gantrez S-97 and Plasdone. Its composition is shown in Table 3 below.

TABLE 3

| Propranolol HCl | 50% |
|---|---|
| Gantrez S-97 + Plasdone | 40% |
| Calcium Sulfate | 9.5% |
| Magnesium Stearate | 0.5% |

Preparation of a Drug-Containing Composition The Active Ingredient (Drug)

Any of the drugs used to treat the body, both topical and systemic, can be incorporated as the active agent in the polymeric carrier of this invention. "Drug" is used herein in its broadest sense as including any composition of matter that will produce a pharmacological or biological response.

Suitable drugs for use in therapy according to this invention include, without limitations; those listed in U.S. Pat. No. 3,732,865 (columns 10 and 11).

Other drugs having the same or different physiological activity as those recited above can be employed in carriers within the scope of the present invention. Suitable mixtures of drugs can, of course, be dispensed with equal facility as with single component systems.

Drugs can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartarate, salicylate, etc. For acidic drugs, salts of metals, amines, or organic cations (e.g. quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the carrier varies widely depending on the particular drug. The desired therapeutic effect, and the time span for which it takes the drug to be released. Since a variety of carriers in a variety of sizes and shapes are intended to provide complete dosage regimen for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

Preferred drugs to be incorporated according to the present invention are those designed for long-term treatment so that multiple daily doses can be avoided. For example, smooth muscle relaxants, e.g. theophylline, anabolics, e.g. methandrostenolone; analgesics, e.g. acetylsalicyclic acid, phenylbutazone or methadone; androgens, e.g. methyltestosterone; antibiotics, e.g. rifampin; antidepressants, e.g. imipramine or maprotiline; antidiabetics, e.g. phenformin; anticonvulsives, e.g. cabamazepine, antihistamines, e.g. tripelennamine; antihypertensives, e.g. hydrolazine; antiinfectives, e.g. trimethoprim; antiparasitics, e.g. nifurimox; antiparkinson agents, e.g. levodopa; antiphlogistics, e.g. naproxen; antitussives, e.g. benzostate; appetite depressants, e.g. mazndol; bronchodilators, e.g. fenoterol; coronary dilators, e.g. fenalcomine; corticoids, e.g. dexamethasone; cytostatics, e.g. floxuridine; diuretics, e.g. hydrochlorothiazide; hypnotics, e.g. glutethimide; neuroleptics, e.g. reserpine or thioridazine; psychoanaleptics, e.g. methylpenidate; tranquilizers, e.g. diazepam; uricosutics, e.g. sulfinpyrazone; vasodilators, e.g. isoproterenol.

Among the most preferred drugs are naproxen sodium, diclofenac sodium, baclofen, metropolol.HCl, beta blockers, such as oxprenolol and propanolol; calcium channel blockers, such as Nifedipine and Verapamil, and anti-asthmatics, such as theophylline.

While the invention has been described with particular reference to certain embodiments thereof, it will be understood that changes and modifications may be made which are within the skill of the art. Accordingly, it is intended to be bound only by the following claims, in which:

What is claimed is:

1. A controlled-release, drug delivery tableted composition consisting essentially of,
   (a) a complex formed by hydrogen bonding in water between poly(maleic diacid-alkyl vinyl ether) and polyvinylpyrrolidone, in about a 1:1 molar ratio and
   (b) an effective amount of a pharmaceutical medicament, which remains substantially insoluble under aqueous acidic conditions and only slowly dissolves in aqueous alkaline medium.

2. A composition according to claim 1 wherein said alkyl vinyl ether is methyl vinyl ether.

3. A tableted composition according to claim 1 which is formed by direct compression, or wet granulation.

4. A composition according to claim 1 wherein the complex is present in an amount of about 30–70% by weight therein.

5. A composition according to claim 1 which includes an ionotropic agent.

6. A composition according to claim 5 in which said agent is calcium sulfate.

* * * * *